United States Patent [19]
Ohgi et al.

[11] Patent Number: 5,885,992
[45] Date of Patent: Mar. 23, 1999

[54] TRITERPENE DERIVATIVE AND MEDICINAL COMPOSITION

[75] Inventors: Tadaaki Ohgi, Shiga; Hiroto Yoshifusa, Osaka; Kazuhisa Kandori, Kyoto, all of Japan

[73] Assignee: Nippon Shinyaku Company, Limited, Kyoto, Japan

[21] Appl. No.: 750,896

[22] PCT Filed: Jun. 22, 1995

[86] PCT No.: PCT/JP95/01249
 § 371 Date: Dec. 19, 1996
 § 102(e) Date: Dec. 19, 1996

[87] PCT Pub. No.: WO96/00236
 PCT Pub. Date: Jan. 4, 1996

[30] Foreign Application Priority Data

Jun. 24, 1994 [JP] Japan .................................. 6-142708

[51] Int. Cl.[6] .......................... A61K 31/53; A61K 31/35; C07C 69/76; C07C 61/12
[52] U.S. Cl. .............................. 514/245; 514/460; 560/8; 560/129; 562/498
[58] Field of Search .................................. 514/245, 460; 560/8, 129; 562/498

[56] References Cited

PUBLICATIONS

Chem. Pharm. Bull., 3340–3346(1982).
Studies on the Constituents of *Clematis* Species. V. On the Saponins of the Root of *Clematis chinensis* Osbeck, by Haruhisa Kizu and Tsuyoshi Tomimori.
Chem. Pharm. Bull., 1935–1939 (1972).
Seed Saponins of *Akebia quinata* Decne. I. Hederagenin 3–0–Glycosides, by Ryuichi Higuchi, Kazumoto Miyahara, and Toshio Kawasaki.
Indian Journal of Chemistry, vol. 29B, 425–429 (May 1990). Cetyltrimethylammonium bromide catalysed sodium periodate oxidation of olean–12–en–28–ols and urs–12–en–28–ols: Construction of Δ[11]–13β, 28–epoxy system of saikogenins: Partial synthesis of 16–deoxysaikogenin–F†, by Rita Mehrotra, Chandan Singh and Satya Pal Popli.
Photochemistry, 615–621 (1984).
ENT–Labdane–Type Diterpene Glucosides form Leaves of *Rubus Chingii*, by Takashi Tanaka, Keiko Kawamura, Takumi Kitahara, Hiroshi Kohda and Osamu Tanaka.
Chem. Pharm. Bull., 2388–2393 (1979).
Studies on the Constituents of *Clematis* Species. I. On the Saponins of the Root of *Clematis chinensis* Osbeck, by Haruhisa Kizu and Tsuyoshi Tomimori.
Tetrahedron, vol. 49, No. 33, 7193–7214 (1993).
The Invention of Radical Reactions. XXXI. Diphenylsilane: A Reagent for Deoxygenation of Alcohols via Their Thiocarbonyl Derivatives, Deamination via Isonitriles, and Dehalogenation of Bromo– and Iodo–Compounds by Radical Chain Chemistry, by Derek H.R. Barton, Doo Ok Jang and Joseph Cs. Jaszberenyi.

Bulletin de la Société Royale des Sciences de Liège, 245–252 (1973).
Contribution a L'étude Chimique des Saponines d'une Sapindacéée Africaine: Eriocoelum Microspermum Radlk. ex de Wild, by C. Delaude and M. Davreux.
J.C.S. Chem. Comm., 1136–1137 (1981).
The Synthesis and Properties of a Series of Strong but Hindered Organic Bases, by Derek H.R. Barton, John D. Elliott, and Stephen D. Géro.
Chem. Pharm. Bull 24(6), 1314–1323 (1976).
Pericarp Saponins of *Akebia quinata* Decne. II. Arjunolic and Norarjunolic Acids, and Their Glycosides, by Ryuichi Higuchi and Toshio Kawasaki, Chem. Pharm. Bull 24(6), 1976.
Chem. Pharm. Bull 24(5), 1021–1032 (1976).
Pericarp Saponins of *Akebia quinata* Decne. I. Glycosides of Hederagenin and Oleanolic Acid, by Ryuichi Higuchi and Toshio Kawasaki, Chem.
J. Chem. Soc., Chem. Commun., 939–941 (1983).
New and Improved Methods for the Radical Decarboxylation of Acids, by Derek H.R. Barton, David Crich, and William B. Motherwell.

(List continued on next page.)

Primary Examiner—Rebecca Cook
Attorney, Agent, or Firm—Graham & James LLP

[57] ABSTRACT

The invention is composed of a hederagenin derivative of the following formula or a pharmaceutically acceptable salt thereof, and a pharmaceutical composition comprising of this compound as an active ingredient.

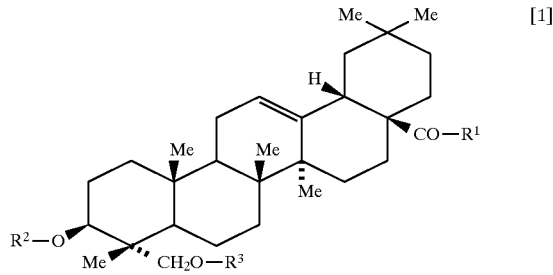

[1]

(wherein $R^1$ represents $OR^{11}$ or $NR^{11}R^{12}$. $R^{11}$ and $R^{12}$ may be the same or different and each represents hydrogen, alkyl that may be substituted, cycloalkyl that may be substituted, alkenyl that may be substituted, alkinyl that may be substituted, aryl that may be substituted, or a heteroaromatic group that may be substituted, $R^2$ and $R^3$ may be the same or different and each represents hydrogen, alkyl that may be substituted, cycloalkyl that may be substituted, alkenyl that may be substituted, alkinyl that may be substituted, acyl that may be substituted, monoalkylcarbamoyl that may be substituted, dialkylcarbamoyl that may be substituted, or alkoxycarbonyl that may be substituted, or $R^2$ and $R^3$ taken together represents carbonyl.)

The pharmaceutical composition of the invention is effective for the therapy of nephritis.

18 Claims, No Drawings

PUBLICATIONS

Choi et al, Planta Medica, 53(1), 62–65 (1987).
Barton et al. J.C.S. Chem. Comm., 15 732–733 (1980).
Madhusudanan et al, Indian J. Chem., Sect. B., 223 370–373 (1983).

CA 122:205207, Zheng et al, Feb. 9, 1995.
CA 121:150765, Kreppel et al, 1994.
CA 124:278388, Morota et al, 1995.
CA 122:203207, Zheng et al, Feb. 9, 1995.
CA 120:263529, Tauleneek et al, 1994.
Reg. No 6055–17–0, none avail.

TRITERPENE DERIVATIVE AND MEDICINAL COMPOSITION

This is 371 of PCT/JP95/01249 filed Jun. 22, 1995.

TECHNICAL FIELD

The present invention relates to a hederagenin derivative, its pharmacologically acceptable salt, and a solvate of either of said derivative and salt, which are of value as medicines.

The compounds according to the present invention have inhibitory activity of mesangial cell proliferation and are useful for the treatment of nephritis.

BACKGROUND TECHNOLOGY

According to the site of principal lesions, nephritis is classified into glomerulonephritis, interstitial nephritis and pyelonephritis, for instance. The most representative of all is glomerulonephritis in which the glomerular tuft is the affected site. Today, nephritis is synonymous with glomerulonephritis (Medical Dictionary, 1st ed., 570, 1987).

Histopathological findings which are most frequently obtained in human glomerulonephritis and considered to be of prognostic importance are mesangial cell proliferation and hyperplasia of the matrix produced by mesangial cells (hereinafter referred to as mesangial matrix). These findings are noted in nearly all types of proliferative glomerulonephritis, inclusive of IgA nephropathy, membranous proliferative glomerulonephritis, and lupus nephritis, in common (Iida: Kindney and Dialysis, 35, 505–509, 1993). And as the mesangial cell proliferation and associated production of mesangial matrix progress, the glomeruli fall into a terminal stage, so call glomerulosclerosis. Therefore, any compound that inhibits mesangial cell proliferation and production of mesangial matrix is of great value as a therapeutic agent for glomerulonephritis.

Two processes are known for mesangial cell proliferation in glomerulonephritis. In the first process, the complement, platelets, and infiltrating cells are involved. Thus, deposition of the immune complexes produced by immunological mechanisms on the glomeruli takes place in situ and activation of the complement and platelets and infiltration of macrophages and neutrophils then occur. These cells release a variety of growth factors and cytokines to activate the mesangial cells and stimulate their proliferation. The second process is a process wish which mesangial cells themselves are associated. Thus, it is a process in which activated mesangial cells themselves release a variety of growth factors and cytokines and the cells releasing them and the adjacent mesangial cells become activated or proliferate. Thus, mesangial cells are activated and proliferate through a complex system consisting of a plurality of processes.

Therefore, when the treatment of glomerulonephritis is considered, it is inconceivable that the mesangial cell proliferation can be sufficiently inhibited even if a given stage in first process mentioned above, for example the stage mediated by the complement and platelets, is inhibited. In fact, it is reported that administration of an antiplatelet drug alone is therapeutically little effective for human nephritis in active stage (Dohi et al., Clinics All-round, 38, 865–870, 1989).

It is known that, among natural substances of the plant origin, there exist compounds having antinephritic activity. For example, the usefulness of pentacyclic triterpene derivatives in the treatment of nephritis and other diseases is indicated in Japanese Laid-Open S61-37749 (an oleanene derivative), Japanese Laid-Open S61-85344 (an oleanene derivative), Japanese Laid-Open H2-73012 (a bryonolic acid derivative), Japanese Laid-Open H4-290846 (a bryonolic acid derivative), and Japanese Laid-Open S61-43141 (a lupane derivative). However, there is no disclosure of an experimental example demonstrating the utility of such compounds in the treatment of nephritis, nor is there a suggestion that they ever have mesangial cell proliferation inhibitory activity.

Hederagenin (3β,23-dihydroxyolean-12-en-28-oic acid) according to the present invention is a pentacyclic triterpene derivative available from natural sources such as *Sapindus mukorossi, Hedera rhombea, Hedera helix, Fatsia japonica*, etc. Hederagenin is known to have hypotensive, antispasmodic (Ann. Pharm. Fr., 30, 555, 1972), hair growth-promoting, dermal aging inhibitory (FR 2669225), antimycotic (Ann. Pharm. Fr., 38, 545, 1980), antiinflammatory (Chem. Pharm. Bull., 28, 1183, 1980), antitrematoid (Rastit. Resur., 28, 103, 1992), antiulcer, antiallergic (Proc. Asian. Symp. Med. Plants Spices, 4th, Meeting Date 1980, Volume 1, 59), anti-suntan (Japanese Laid-Open H1-42411), deodorant, and hyperhidrosis inhibitory (FR 2541895), and other activities but it is not known that the compound is useful for the treatment of nephritis.

As hederagenin derivatives, the following compounds (1)–(15) are already known but it is not known whether they are of use as medicines for the treatment of nephritis or other diseases.

(1) 3β-Hydroxy-23(4α)-acetoxyolean-12-en-28-oic acid (Chem. Pharm. Bull., (1976), 24(6), 1314).

(2) 3β-Hydroxy-23(4α)-methoxyolean-12-en-28-oic acid (Chem. Pharm. Bull., (1976), 24(5), 1021).

(3) 3β,23(4α)-diacetoxyolean-12-en-28-oic acid (J. Chem. Soc., Chem. Commun., (1983), (17), 939).

(4) 3β,23(4α)-dibenzoyloxyolean-12-en-28-oic acid (Bull. Soc. Roy. Sci. Liege, (1973), 42(5-6), 245).

(5) 3β,23(4α)-diformyloxyolean-12-en-28-oic acid (CAS, Registry No.=6055-17-0).

(6) Methyl 3β,23(4α)-dihydroxyolean-12-en-28-oate (J. Chem. Soc., Chem. Commun., (1981), (21), 1136).

(7) Methyl 3β-hydroxy-23(4α)-acetoxyolean-12-en-28-oate (Phytochemistry, (1984), 23(3), 615).

(8) Methyl 3β-hydroxy-23(4α)-methoxyolean-12-en-28-oate (Chem. Pharm. Bull., (1979), 27(10), 2388).

(9) Methyl 3β-acetoxy-23(4α)-hydroxyolean-12-en-28-oate (Tetrahedron, (1993), 49(33), 7193).

(10) Methyl 3β-benzoyloxy-23(4α)-hydroxyolean-12-en-28-oate (Tetrahedron, (1993), 49(33), 7193).

(11) Methyl 3β-methoxy-23(4α)-hydroxyolean-12-en-28-oate (Chem. Pharm. Bull., (1982), 30(9), 3340).

(12) Methyl 3β,23(4α)-diacetoxyolean-12-en-28-oate (Chem. Pharm. Bull., (1982), 30(9), 3340).

(13) Methyl 3β-acetoxy-23(4α)-methoxyolean-12-en-28-oate (Chem. Pharm. Bull., (1972), 20(9), 1935).

(14) Methyl 3β,23(4α)-dibenzoyloxyolean-12-en-28-oate (Bull. Soc. Roy. Sci. Liege, (1973), 42(5-6), 245).

(15) Methyl 3β,23(4α)-dimethoxyolean-12-en-28-oate (Indian J. Chem., Sect. B. (1990), 29B(5), 425).

DISCLOSURE OF THE INVENTION

It is obvious from the foregoing that any compound having mesangial cell growth inhibitory activity can be an excellent therapeutic agent for nephritis. The inventors of the present invention had been doing a series of investigations in search of such compounds.

As a result, the inventors discovered that a specific class of hederagenin derivatives have high mesangial cell proliferation inhibitory activity and have perfected the present invention.

The present invention is directed to a pharmaceutical composition for the therapy of nephritis which comprises a hederagenin derivative of the following formula [1] or a pharmacologically acceptable salt thereof, or a solvate of either of them, as an active ingredient and to novel compounds.

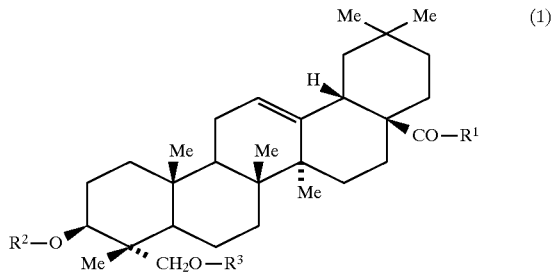

wherein $R^1$ represents $OR^{11}$ or $NR^{11}R^{12}$. $R^{11}$ and $R^{12}$ may be the same or different and each represents (1) hydrogen, (2) alkyl that may be substituted, (3) cycloalkyl that may be substituted, (4) alkenyl that may be substituted, (5) alkinyl that may be substituted, (6) aryl that may be substituted, or (7) a heteroaromatic group that may be substituted.

$R^2$ and $R^3$ may be the same or different and each represents (1) hydrogen, (2) alkyl that may be substituted, (3) cycloalkyl that may be substituted, (4) alkenyl that may be substituted, (5) alkinyl that may be substituted, (6) acyl that may be substituted, (7) monoalkylcarbamoyl that may be substituted, (8) dialkylcarbamoyl that may be substituted, or (9) alkoxycarbonyl that may be substituted, or $R^2$ and $R^3$, taken together, represents carbonyl.

Substituents on $R^{11}$, $R^{12}$, $R^2$, and $R^3$ may be the same or different and are respectively selected from among (1) halogen, (2) $OR^{13}$, (3) $OCOR^{13}$, (4) $COOR^{13}$, (5) cyano, (6) $NR^{13}R^{14}$, (7) cycloalkyl, (8) aryl that may be substituted by halogen, alkyl, hydroxy, or amino, and (9) heteroaromatic groups that may be substituted by halogen, alkyl, hydroxy, or amino. $R^{13}$ and $R^{14}$ may be the same or different and each represents (1) hydrogen or (2) alkyl that may be substituted by hydroxy, alkoxy, amino, monoalkylamino, or dialkylamino.

Among the hederagenin derivatives of formula [I], the compound in which $R^1$ is hydroxy, $R^2$ is hydrogen, and $R^3$ is hydrogen is a known naturally-occurring substance called hederagenin, which is distinct in chemical structure from the above-mentioned pentacyclic triterpene derivatives claimed to be useful for the treatment of nephritis. For example, whereas olean-12-en-3β,22β,23(4β)-triol, which is described in Japanese Laid-Open S61-37749, has hydroxy as a substituent on 22-position, hydroxy in 23-position, which is β-oriented, and methyl in 28-position, hederagenin is unsubstituted in 22-position and has hydroxy in 23-position, which is α-oriented, and carboxyl in 28-position. Thus, there are differences in chemical structure.

While hederagenin was known to possess a variety of physiological actions as mentioned above, it has not been known that this substance is useful for the treatment of nephritis.

Among the hederagenin derivatives of formula [I], compounds excluding the following cases (1)–(5) are novel compounds not heretofore described in the literature.

(1) $R^1$ is hydroxy or methoxy, $R^2$ is hydrogen, and $R^3$ is hydrogen, acetyl, or methyl.
(2) $R^1$ is hydroxy and each of $R^2$ and $R^3$ is formyl, acetyl, or benzoyl.
(3) $R^1$ is methoxy, $R^2$ is acetyl, and $R^3$ is hydrogen, acetyl, or methyl.
(4) $R^1$ is methoxy, $R^2$ is benzoyl, and $R^3$ is hydrogen or benzoyl.
(5) $R^1$ is methoxy, $R^2$ is methyl, and $R^3$ is hydrogen or methyl.

The present invention is characterized by the finding that compounds of formula [I] have mesangial cell proliferation inhibitory activity and are useful for the treatment of nephritis.

The terms used in the present invention are explained below.

"Alkyl" means a straight-chain or branched-chain alkyl group of 1–7 carbon atoms, thus including methyl, ethyl, n-propyl, isopropyl, n-butyl, isobutyl, sec-butyl, tert-butyl, n-pentyl, isopentyl, n-hexyl, isohexyl, n-heptyl, isoheptyl, etc. Particularly preferred are straight-chain groups containing 1–3 carbon atoms, e.g. methyl, ethyl, and n-propyl.

"Cycloalkyl" means a cycloalkyl group of 3–7 carbon atoms, such as cyclopropyl, cyclobutyl, cyclopentyl, cyclohexyl, cycloheptyl, etc.

"Alkenyl" means a straight-chain or branched-chain alkenyl group of 2–7 carbon atoms, thus including vinyl, 1-propenyl, isopropenyl, allyl, 1-butenyl, 3-butenyl, 1-pentenyl, 4-pentenyl, 1-hexenyl, 5-hexenyl, 1-heptenyl, 6-heptenyl, etc.

"Alkinyl" means a straight-chain or branched-chain alkinyl group of 2–7 carbon atoms, such as ethinyl, 1-propinyl, 2-propinyl, 1-butinyl, 3-butinyl, 1-pentinyl, 4-pentinyl, 1-hexinyl, 5-hexinyl, 1-heptinyl, 6-heptinyl, etc.

"Aryl" means an aryl group of 6–10 carbon atoms, such as phenyl, 1-naphthyl, 2-naphthyl, etc.

"Heteroaromatic group" means a 5- or 6-membered aromatic group having 1–4 hetero-atoms selected from among nitrogen, oxygen, and sulfur, thus including 1-pyrrolyl, 2-pyrrolyl, 3-pyrrolyl, 2-furanyl, 3-furanyl, 2-thienyl, 3-thienyl, 2-oxazolyl, 2-thiazolyl, 1H-1,2,4-triazol-1-yl, 1H-tetrazol-5-yl, 2-pyridyl, 3-pyridyl, 4-pyridyl, 2-pyrimidinyl, 4-pyrimidinyl, 2-pyrazinyl, 1,3,5-triazin-2-yl, etc.

"Halogen" means fluorine, chlorine, bromine, and iodine.

"Acyl" means "alkylcarbonyl" and "arylcarbonyl". The alkyl moiety of "alkylcarbonyl" is the alkyl mentioned above. The aryl moiety of "arylcarbonyl" is the aryl mentioned above. "Acyl" specifically includes acetyl, propionyl, butyryl, isobutyryl, benzoyl, 1-naphthoyl, 2-naphthoyl, etc.

The alkyl moieties of "alkoxy", "alkoxycarbonyl", "monoalkylcarbamoyl", and "dialkylcarbamoyl" may be the same or different alkyl groups mentioned hereinbefore.

Among compounds [1] of the present invention, preferred compounds as therapeutic agents for nephritis belong to any of the following compound groups (1)–(5).
(1) Compounds in which $R^1$ is hydroxy, acyloxyalkoxy, phenylalkoxy, alkoxyalkoxy, hydroxyalkoxy, haloalkoxy, di(hydroxyalkyl)aminoalkoxy, (alkoxyalkyl)amino, halogen-substituted phenylamino, (dialkylaminoalkyl) amino, [di(hydroxyalkyl)aminoalkyl]amino, (carboxyalkyl)amino, (alkoxycarbonylalkyl) amino, (cyanoalkyl) amino, or di-amino-substituted triazinylalkylamino, $R^2$ is hydrogen, and $R^3$ is hydrogen.
(2) Compounds in which $R^1$ is hydroxy, (alkoxyalkyl)amino, halogen-substituted phenylamino, (dialkylaminoalkyl) amino, [di(hydroxyalkyl)aminoalkyl]amino, (alkoxycarbonylalkyl)amino, or (cyanoalkyl)amino, $R^2$ is acetoxy, and $R^3$ is acetoxy.
(3) Compounds in which $R^1$ is phenylalkoxy, $R^2$ is hydroxy, (alkoxycarbonylalkyl)carbamoyl, or (alkoxyalkyl) carbamoyl, and $R^3$ is phenylalkyl.
(4) Compounds in which $R^1$ is hydroxy, $R^2$ is (alkoxycarbonylalkyl)carbamoyl or (alkoxyalkyl) carbamoyl, and $R^3$ is hydrogen.

(5) Compounds in which $R^1$ is hydroxy or acyloxyalkoxy and $R^2$ and $R^3$ taken together represents carbonyl.

Among compounds [1] of the present invention, still more preferred as therapeutic agents for nephritis are compounds in which $R^1$ is hydroxy, (alkoxyalkyl)amino, or acyloxyalkoxy, $R^2$ is hydrogen, and $R^3$ is hydrogen.

Particularly preferred as therapeutic agents for nephritis among compounds [1] are compounds wherein $R^1$ is hydroxy, 2-methoxyethylamino, or 2-acetoxyethoxy, $R^2$ is hydrogen, and $R^3$ is hydrogen.

Hederagenin can be obtained typically by the following method.

*Sapindus mukorossi* Gaertn., either as it is, dried, or dried and crushed, is hot-extracted using water, alcohol (e.g. methanol, ethanol, isopropyl alcohol, etc.), or aqueous alcohol as a solvent at 50° to 80° C. for 1–4 hours and the extract is concentrated under reduced pressure at a temperature not exceeding 60° C. to provide an extract.

To the extract thus obtained is added a 1–5% solution of mineral acid (e.g. hydrochloric acid, sulfuric acid, or nitric acid) in alcohol (e.g. methanol, ethanol, isopropyl alcohol, etc.) and the mixture is refluxed for hydrolysis for 1–3 hours. After the completion of the hydrolysis, the reaction mixture is adjusted to pH 6–7 with alkali (e.g. potassium hydroxide, sodium hydroxide, etc.). This alcoholic solution can be purified by adding activated carbon and heating. Hederagenin can be obtained by concentrating the alcoholic solution under reduced pressure. The hederagenin thus obtained can be purified by washing with a suitable solvent such as acetonitrile, ethanol, or the like, recrystallization, column chromatography, thin-layer chromatography, etc.

Hederagenin has 3 functional groups, namely a carboxyl group and two hydroxy groups. Starting with hederagenin, the desired hederagenin derivative [1] can be produced by utilizing the differences in reactivity of these functional groups.

Starting with hederagenin (the compound in which $R^1$=OH, $R^2$=H, $R^3$=H), derivatives in 28-position ($R^1 \neq$OH, $R^2$=H, $R^3$=H) can be produced by the following "1. Reaction of the carboxy".

Starting with this derivative in 28-position, derivatives in 23- and 28-position ($R^1 \neq$OH, $R^2$=H, $R^3 \neq$H) can be produced by the following "2. Reaction of the hydroxy in 23-position".

Starting with a derivative in 23- and 28-position, derivatives in 3β-, 23- and 28-position ($R^1 \neq$OH, $R^2 \neq$H, $R^3 \neq$H) can be produced by the following "3. Reaction of the hydroxy in 3β-position".

Starting with a derivative in 28-position carrying a protective group in 28-position, derivatives in 23-position ($R^1$=OH, $R^2$=H, $R^3 \neq$H) can be produced by preparing a derivative in 23- and 28-position according to the following "2. Reaction of the hydroxy in 23-position" and, then, deprotecting in 28-position.

Starting with a derivative in 23- and 28-position carrying a protective group in each of 23- and-28-positions, derivatives in 3β-position ($R^1$=OH, $R^2 \neq$H, $R^3$=H) can be produced by preparing a derivative in 3β-, 23- and 28-position according to the following "3. Reaction of hydroxy in 3β-position" and, then, deprotecting in the 23- and 28-position.

Starting with a derivative in 23- and 28-position carrying a protective group in 28-position only, derivatives in 3β- and 23-position ($R^1$=OH, $R^2 \neq$H, $R^3 \neq$H) can be produced by preparing a derivative 3β-, 23- and 28-position according to the following "3. Reaction of hydroxy in 3β-position" and, then, deprotecting in the 28-position.

Starting with a derivative in 23- and 28-position carrying a protective group in 23-position only, derivatives in 3β- and 28-position ($R^1 \neq$OH, $R^2 \neq$H, $R^3$=H) can be produced by preparing a derivative in 3β-, 23- and 28-position according to the following "3. Reaction of hydroxy in 3β-position" and, then, deprotecting in 23-position.

Starting with hederagenin ($R^1$=OH, $R^2$=H, $R^3$=H), derivatives in 3β-and 23-position ($R^1$=OH, $R^2 \neq$H, $R^3 \neq$H) can be produced by the following "4. Reaction of dihydroxy in 3β-and 23-position".

Starting with a derivative in 28-position ($R^1 \neq$OH, $R^2$=H, $R^3$=H), derivatives in 3β-, 23- and 28-position ($R^1 \neq$OH, $R^2 \neq$H, $R^3 \neq$H) can be produced by the following "4. Reaction of dihydroxy in 3β- and 23-position".

1. Reaction of carboxy

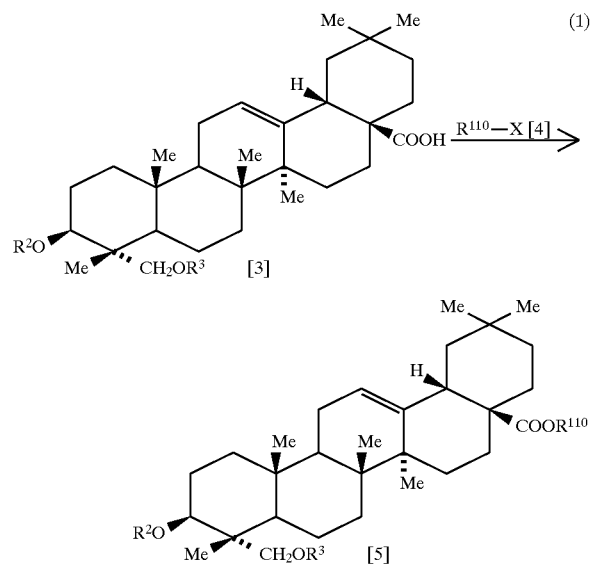

[wherein $R^2$ and $R^3$ are as defined hereinbefore. $R^{110}$ represents $R^{11}$ except hydrogen, X represents a leaving group such as halogen, e.g. chlorine, bromine, iodine, etc., alkylsulfoxy such as methanesulfoxy, and arylsulfoxy such as toluenesulfoxy.]

By reacting carboxylic acid [3] with compound [4], ester [5] can be produced. This reaction can be generally conducted in the absence of a solvent or in the presence of an aprotic solvent (polar solvents such as acetonitrile, N,N-dimethyl-formamide (DMF), etc., ether series solvents such as tetrahydrofuran (THF), diethyl ether, etc., halogenated hydrocarbon series solvents such as chloroform, methylene chloride, etc., hydrocarbon series solvents such as benzene, toluene, n-hexane, etc., and mixtures of said solvents) in the presence of a base (e.g. potassium carbonate, sodium carbonate, sodium hydrogen carbonate, potassium hydrogen carbonate, pyridine, 4-dimethylaminopyridine, triethylamine, sodium hydride, etc.) at −20° to 100° C. The reaction time depends on the species of compound [3] and compound [4] and the reaction temperature used, but generally may suitably be 30 minutes–24 hours. The preferred proportion of compound [4] relative to compound [3] is 1–1.2 molar equivalents.

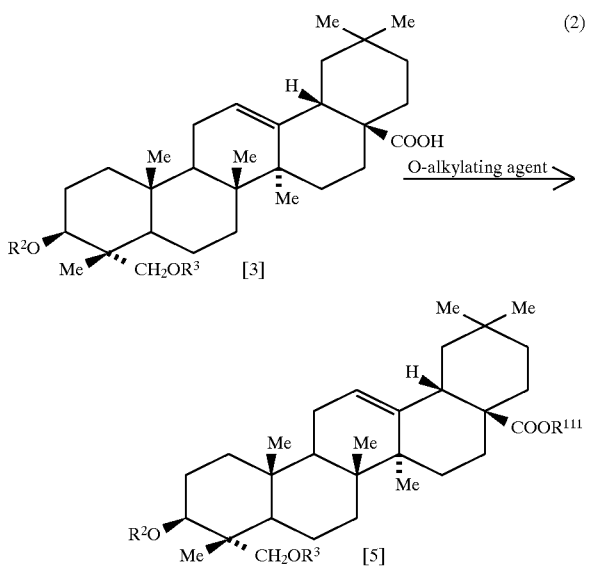

[wherein $R^2$ and $R^3$ are as defined above. $R^{111}$ represents unsubstituted alkyl]

By reacting carboxylic acid [3] with an O-alkylating agent, ester [5] can be produced. The O-alkylating agent that can be used includes diazoalkanes (e.g. diazomethane, diazoethane, etc.), trimethylsilyldiazomethane, and ortho-esters (ethyl orthoformate, ethyl orthoacetate, etc.), among others. This reaction can be generally conducted in the absence of a solvent or in an aprotic solvent such as the one mentioned above. The reaction temperature depends on the species of O-alkylating agent. Thus, the temperature range of −20° to 30° C. is suitable for diazoalkanes and trimethylsilyldiazomethane and the range of 100° to 200° C. is suitable for ortho-esters. The reaction time which depends on the species of compound [3] and O-alkylating agent and the reaction temperature used, but the range of 1 minute to 24 hours is generally suitable. The preferred proportion of the O-alkylating agent relative to compound [3] is 1–1.2 molar equivalents.

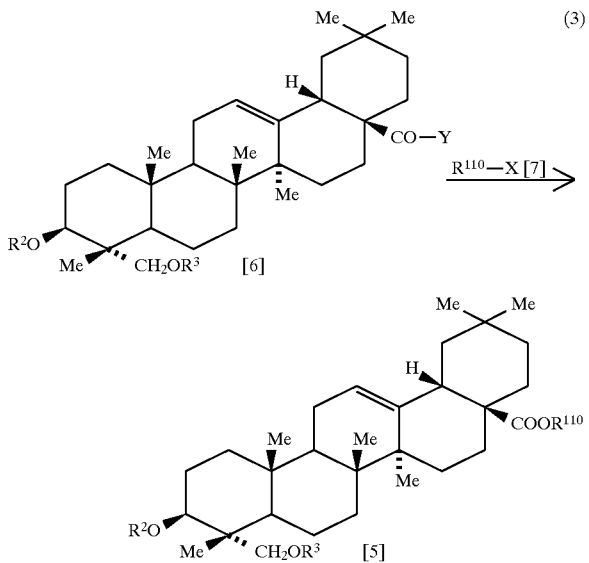

[wherein $R^2$, $R^3$, and $R^{110}$ are as defined above. Y represents hydroxy or a leaving group, e.g. halogen such as chlorine, bromine, iodine, etc., alkoxy such as methoxy etc., aryloxy such as p-nitrophenoxy etc., alkylsulfoxy such as methanesulfoxy, etc., arylsulfoxy such as toluenesulfoxy etc., imidazolyl, alkylcarboxy, or arylcarboxy.]

By reacting compound [6] with alcohol [7], ester [5] can be produced.

Thus, ester [5] can be produced by reacting compound [6] (Y is not hydroxy but said leaving group), such as an acid halide (e.g. acid chloride, acid bromide, etc.), alkyl ester (e.g. methyl ester, ethyl ester, etc.), active ester (e.g. p-nitrophenyl ester, p-chlorophenyl ester, etc.), imidazolide, or mixed acid anhydride (e.g. mixed acid anhydrides with monoalkyl carbonates, mixed acid anhydrides with alkyl phosphates) with alcohol [7] in a suitable manner or alternatively by condensing compound [6] (where Y is hydroxy) directly with compound [7] using a condensing agent (e.g. 1-ethyl-3-(3-dimethylamino-propyl)carbodiimide, dicyclohexylcarbodiimide, 2-chloro-N-methylpyridinium iodide, diphenylphosphoryl azide, diethylphosphoryl cyanide, triphenylphosphine-carbon tetrachloride, etc.).

When an acid halide is used, ester [5] can be produced by conducting the reaction in the same aprotic solvent as above in the presence of the same base as above at −20° to 100° C. The reaction time depends on the species of acid halide and the reaction temperature, but the range of 30 minutes to 24 hours is generally suitable. The preferred proportion of alcohol [7] relative to the acid halide is 1–1.2 molar equivalents.

The acid halide can be prepared by reacting compound [6] (where Y is hydroxy) with a thionyl halide (e.g. thionyl chloride or thionyl bromide) in the absence of a solvent or in the same aprotic solvent as above and in the absence of a base or in the presence of the same base as mentioned above at −20° to 100° C. The reaction time depends on the species of acid halide and the reaction temperature, but the range of 30 minutes to 24 hours is generally suitable. The proportion of the thionyl halide should be at least equimolar to compound [6] (where Y is hydroxy) and can be a large excess, e.g. 10 molar equivalents or more.

When a condensing agent is used, ester [5] can be produced by conducting the reaction in the same aprotic solvent as above and either in the presence of the same base as above or in the absence of a base at −20° to 100° C. The reaction time depends on the species of condensing agent and the reaction temperature used but the range of 30 minutes to 24 hours is generally suitable. The preferred proportion of alcohol [7] and of the condensing agent relative to compound [6] (where Y is hydroxy) is 1–1.2 molar equivalents.

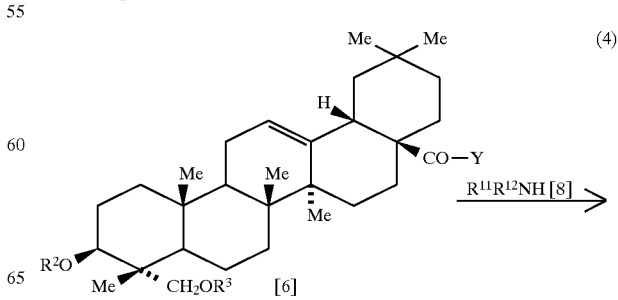

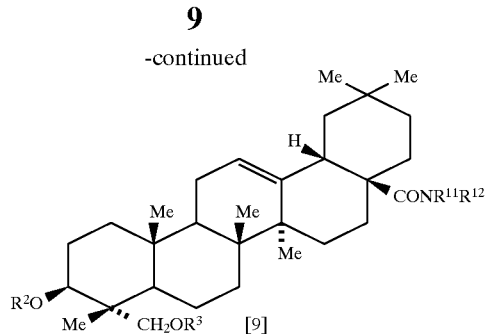

[9]

[wherein $R^2$, $R^3$, $R^{11}$, $R^{12}$, and Y are as defined hereinbefore.]

By reacting compound [6] with amine [8], amide [9] can be produced.

Thus, amide [9] can be produced by reacting compound [6] (where Y is said leaving group except hydroxy), such as an acid halide (e.g. acid chloride, acid bromide, etc.), alkyl ester (e.g. methyl ester, ethyl ester, etc.), active ester (e.g. p-nitrophenyl ester, p-chlorophenyl ester, etc.), imidazolide, or mixed acid anhydride (e.g. mixed acid anhydrides with monoalkyl carbonates, mixed acid anhydrides with alkyl phosphates) with amine [8] in a suitable manner or alternatively condensing compound [6] (where Y is hydroxy) directly with compound [8] using a condensing agent (e.g. 1-ethyl-3-(3-dimethylaminopropyl)carbodiimide, dicyclohexylcarbodiimide, diisopropylcarbodiimide, benzotriazol-1-yl-tris(dimethylamino)-phosphonium hexafluorophosphide, diphenylphosphoryl azide, propane-phosphoric anhydride, etc.) in the presence or absence of an additive (e.g. N-hyroxysuccinimide, 1-hydroxybenzotriazole, 3-hydroxy-4-oxo-3,4-dihydro-1,2,3-triazine, etc.).

When the acid halide is used, amide [9] can be produced by conducting the reaction in the same aprotic solvent as above in the presence of the same base as above at −20° to 100° C. The reaction time depends on the species of acid halide and the reaction temperature used, but the range of 30 minutes to 24 hours is generally preferred. The preferred proportion of amine [8] relative to the acid halide is 1–1.2 molar equivalents.

When a condensing agent is used, amide [9] can be produced by conducting the reaction in the same aprotic solvent as above and in the presence or absence of the same base as above at −20° to 100° C. The reaction time depends on the species of condensing agent and the reaction temperature used, but the range of 30 minutes to 24 hours is generally suitable. The preferred proportion of amine [8] and of the condensing agent relative to compound [6] (where Y is hydroxy) is 1–2 molar equivalents. The amine [8] can be used in excess so that it may function as the base as well.

2. Reaction of hydroxy in 23-position

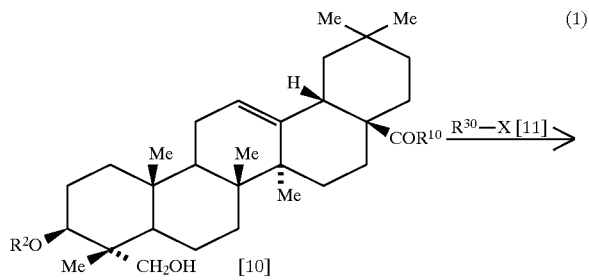

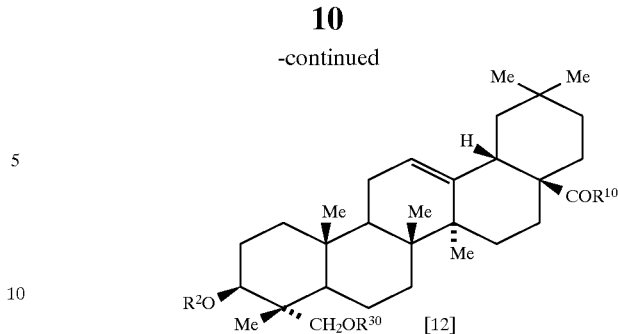

[12]

[wherein $R^2$ and X are as defined hereinbefore; $R^{10}$ represents $R^1$ except hydroxy; $R^{30}$ represents $R^3$ except hydrogen.]

By reacting 23-hydroxy compound [10] with compound [11], compound [12] (e.g. ether, ester, carbonic ester, carbamic ester, etc.) can be produced. This reaction can be generally conducted in the absence of a solvent or in the same aprotic solvent as above in the presence of the same base as above or in the absence of a base at −20° to 100° C. The reaction time depends on the species of compounds [10] and [11] and the reaction temperature used, but the range of 30 minutes to 24 hours is generally suitable. The preferred proportion of compound [11] relative to compound [10] is 1–1.2 molar equivalents.

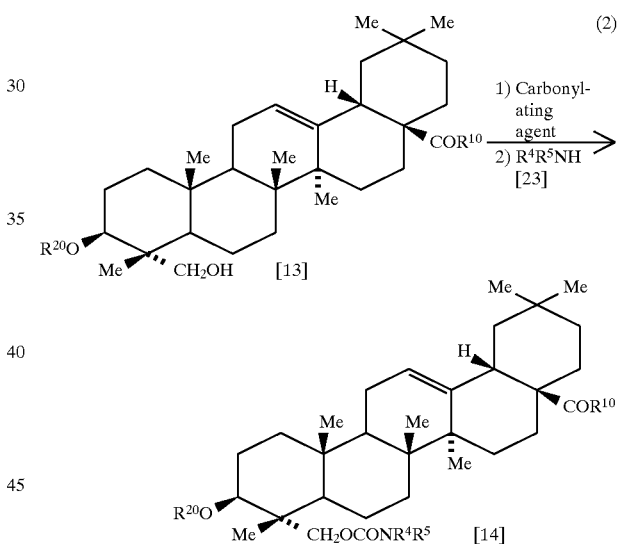

[wherein $R^{10}$ is as defined hereinbefore; $R^{20}$ represents $R^2$ except hydrogen; $R^4$ and $R^5$ may be the same or different and each represents alkyl that may be substituted, the substituent or substituents being selected from among (1) halogen, (2) $OR^6$, (3) $OCOR^6$, (4) $COOR^6$, (5) cyano, (6) $NR^6R^7$, (7) cycloalkyl, (8) aryl that may be substituted by halogen, alkyl, hydroxy, or amino, and (9) heteroaromatic groups that may be substituted by halogen, alkyl, hydroxy, or amino. $R^6$ and $R^7$ may be the same or different and each represents (1) hydrogen or (2) alkyl that may be substituted by hydroxy, alkoxy, amino, monoalkylamino, or dialkylamino.]

By reacting 23-hydroxy compound [13] with a carbonylating agent and, then, with amine [23], carbamic acid ester [14] can be produced.

The carbonylating agent that can be used includes carbonyldiimidazole, p-nitrochloroformates, etc. The preferred proportion of the carbonylating agent and of amine [23] relative to compound [13] is 1–1.2 molar equivalents.

The other reaction conditions are similar to the conditions of the above reaction for producing compound [12] from compounds [10] and [11]. Amine [23] can be used in excess so that it may serve as the base as well.

3. Reaction of hydroxy in 3β-position

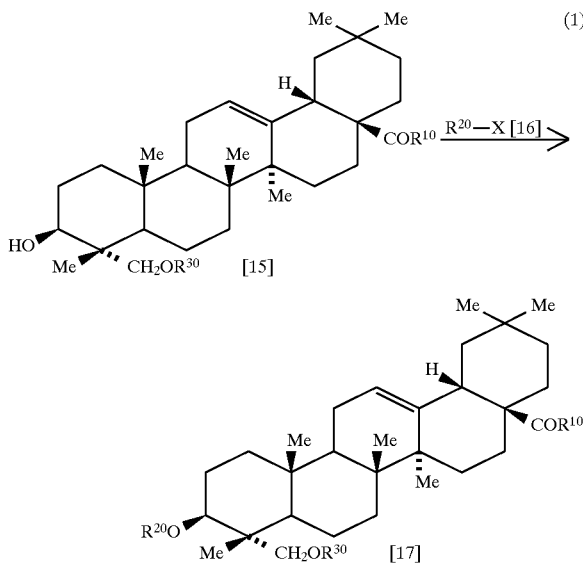

[wherein $R^{10}$, $R^{20}$, $R^{30}$, and X are as defined hereinbefore.]

By reacting 3β-hydroxy compound [15] with compound [16], compound [17] (e.g. ether, ester, carbonic ester, and carbamic ester) can be produced. This reaction can be carried out in the same manner as the above reaction for producing compound [12] from compounds [10] and [11].

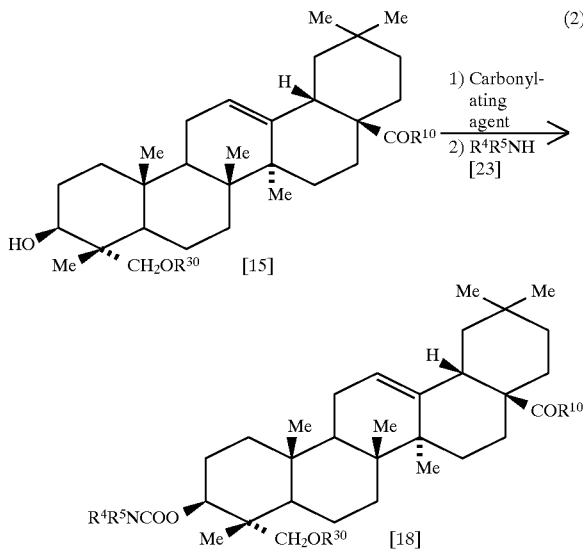

[wherein $R^4$, $R^5$, $R^{10}$, and $R^{30}$ are as defined hereinbefore.]

By reacting hydroxy compound in 23-position [15] with the same carbonylating agent as above and, then, with amine [23], carbamic ester [18] can be produced. This reaction can be carried out in the same manner as the above-mentioned reaction for producing carbamic ester [14] from compound [13], carbonylating agent, and amine [23].

4. Reaction of dihydroxy in 3β- and 23-position

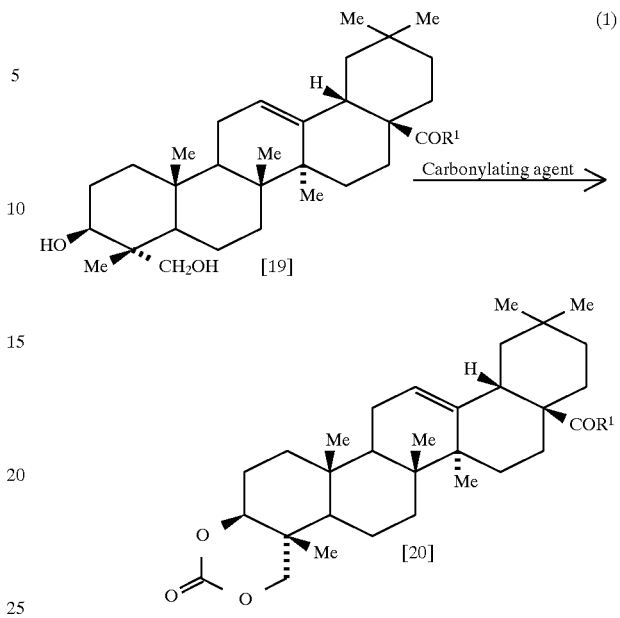

[wherein $R^1$ is as defined hereinbefore.]

By reacting 3β,23-dihydroxy compound [19] with the same carbonylating agent as above, 3β,23-carbonyldioxy compound [20] can be produced. This reaction is generally conducted in the absence of a solvent or in the same aprotic solvent as above in the presence of the same base as above or in the absence of a base at −20° to 100° C. The reaction time depends on the species of compound [19] and carbonylating agent and the reaction temperature used, but the range of 30 minutes to 24 hours is generally suitable. The preferred proportion of the carbonylating agent relative to compound [19] is 1–1.2 molar equivalents.

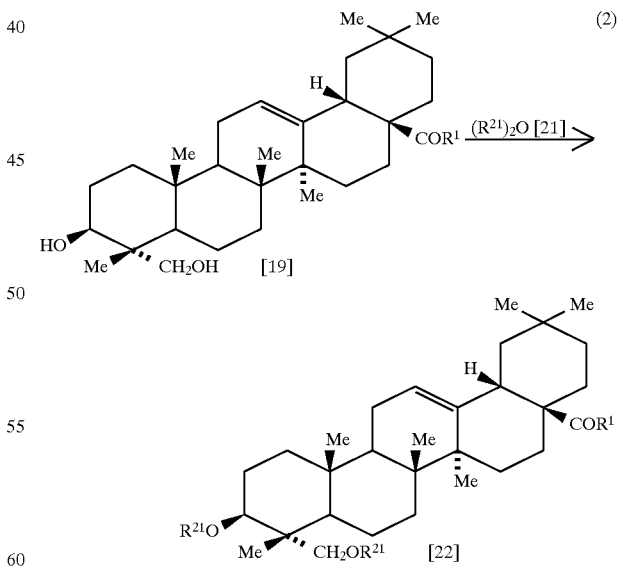

[wherein $R^1$ is as defined hereinbefore. $R^{21}$ represents acyl.]

By reacting 3β,23-dihydroxy compound [19] with carboxylic anhydride [21], 3β,23-diacyloxy compound [22] can be produced. This reaction can be generally conducted in the absence of a solvent or in the same aprotic solvent as above in the presence of the same base as above or in the absence of a base at −20° to 100° C. The reaction time depends on the species of compound [19] and carboxylic anhydride [21] and the reaction temperature used, but the range of 30 minutes to 24 hours is generally suitable. The preferred proportion of carboxylic anhydride [21] relative to compound [19] is 2–2.2 molar equivalents.

In case the starting compounds have substituents (e.g. amino, hydroxy, carboxy, etc.) which should not be involved in the above reactions (1)–(4), the starting compounds can be protected with benzyl, acetyl, tert-butoxycarbonyl, etc. by the per se known procedure before the contemplated reactions are conducted. After completion of the reaction in each case, the protective group or groups can be eliminated by the known procedures such as catalytic reduction, alkaline treatment, acid treatment, etc.

When, in the compound obtained by any of the above reactions, $R^{11}$, $R^{12}$, $R^2$ or $R^3$ is halogen-substituted alkyl, halogen-substituted alkenyl, halogen-substituted alkinyl, or halogen-substituted cycloalkyl, the halogen can be converted, by the known process, to $OR^{13}$ ($R^{13}$ is as defined hereinbefore; J. Org. Chem., 44, 2307 (1979) etc.), $OCOR^{13}$ ($R^{13}$ is as defined hereinbefore; Tetrahedron Lett., 1972, 1853 etc.), $NR^{13}R^{14}$ ($R^{13}$ and $R^{14}$ are as defined hereinbefore; Org. Synth. V, 88 (1973) etc.), or cyano (J. Org. Chem., 25, 877 (1960)).

When the compound obtained by any of the above reactions has cyano, the group can be converted, by the known process, to $COOR^{13}$ ($R^{13}$ is as defined hereinbefore; Org. Synth., III, 557 (1955), Org. Synth. I, 27 (1941), etc.) or a heteroaromatic group such as triazinyl (Org. Synth. IV, 78 (1963)).

When the compound obtained by any of the above-mentioned reactions has alkoxycarbonyl, the group can be converted, by the known process, to carboxy (Org. Synth., IV, 169 (1963), Org. Synth. IV, 608 (1963)).

When the compound obtained by any of the above-mentioned reactions has carboxy, the group can be converted, by the known process, to alkoxycarbonyl (Org. Synth. III, 381 (1955) etc.).

When the compound obtained by any of the above reactions has hydroxy, the group can be converted, by the known process, to $OR^{13}$ ($R^{13}$ has the same meaning as defined hereinbefore but excluding hydrogen; J. Org. Chem., 44, 2307 (1979) etc.) or $OCOR^{13}$ ($R^{13}$ is as defined above; Org. Synth., IV, 263 (1963), Org. Synth., VI, 560 (1988).

When the compound obtained by any of the above reactions has amino, this group can be converted, by the known process, to $NR^{13}R^{14}$ ($R^{13}$ and $R^{14}$ are as defined hereinbefore; Org. Synth., V, 88 (1973) etc.) or a heteroaromatic group such as pyrrole (Org. Synth., II, 219 (1943) etc.).

The hederagenin derivative [1] having carboxy can be used as it is in the free carboxylic acid form for therapeutic purposes but it can be converted to a pharmaceutically acceptable salt by the known procedure and used as such. The salt that can be used includes alkali metal salts such as sodium salt, potassium salt, etc. and alkaline earth metal salts such as calcium salt.

For example, the alkali metal salt of hederagenin derivative [1] can be obtained by adding one equivalent of sodium hydroxide, potassium hydroxide or the like to the carboxy-containing hederagenin derivative [1], preferably in an alcoholic solvent.

The alkaline earth metal salt of hederagenin derivative [1] can be obtained by dissolving an alkali metal salt prepared as above in water, methanol, ethanol, or a mixed solvent thereof and adding one equivalent of, for example, calcium chloride.

The hederagenin derivative [1], either unsubstituted or having substituted amino, can be used as it is in the free amine form for therapeutic purposes but can also be used in the form of a pharmaceutically acceptable salt prepared by the known procedure. The salt that can be used includes salts with mineral acids such as hydrochloric acid, hydrobromic acid, sulfuric acid, phosphoric acid, etc. and salts with organic acids such as acetic acid, citric acid, tartaric acid, maleic acid, succinic acid, fumaric acid, p-toluenesulfonic acid, benzenesulfonic acid, methanesulfonic acid, etc.

For example, the hydrochloride of hederagenin derivative [1] can be obtained by dissolving the hederagenin derivative [1], whether unsubstituted or having substituted amino, in an alcoholic solution of hydrogen chloride.

The compound [1] according to the present invention can be isolated in pure form from the reaction mixture by routine fractional purification techniques such as extraction, concentration, neutralization, filtration, recrystallization, column chromatography, thin-layer chromatography, etc.

The solvate (inclusive of hydrate) of the compound [1] or of the salt of the compound [1] also falls within the scope of the invention. The solvate can be obtained generally by recrystallizing the salvation substrate from the corresponding solvent or a suitable mixed solvent containing the corresponding solvent.

For example, the hydrate of compound [1] according to the present invention can be obtained by recrystallizing the compound [1] of the invention from aqueous alcohol.

The compound [1] according to the present invention may assume polymorphism. The polymorphs in such cases also fall within the scope of the invention.

The present invention covers methods for treating nephritis which comprise administering an effective amount of the compound of formula [1] to human or other animals.

Use of the compound of formula [1] in the manufacture of therapeutic drugs for nephritis also falls within the scope of the invention.

As demonstrated in the test examples presented hereinafter, the compound of the present invention has excellent mesangial cell proliferation inhibitory activity. Moreover, its toxicological potential is low. Therefore, the pharmaceutical composition of the present invention is of value as a very desirable therapeutic drug for nephritis and is effective in the treatment of chronic glomerulonephritis, especially proliferative glomerulonephritis, among various types of nephritis.

For administration as a medicine, the compound of the present invention can be administered, either as it is or in the form of a pharmaceutical composition containing typically 0.1–99.5%, preferably 0.5–90%, of the compound in a medicinally acceptable nontoxic, inert carrier, to animals inclusive of humans.

As the carrier, one or more of solid, semisolid or liquid diluent, filler, and other formulation auxiliaries can be employed. The pharmaceutical composition is preferably administered in unit dosage forms. The pharmaceutical composition of the present invention can be administered intravenously, orally, into the tissue, locally (e.g. transdermally), or rectally. Of course, a dosage form suited for each route of administration should be used. Oral administration is particularly preferred.

The dosage for the pharmaceutical composition for the therapy of nephritis is preferably selected in consideration of patient factors, e.g. age and body weight, route of administration, nature and severity of illness, etc. Generally, however, in terms of the active compound of the invention, the daily dose range of 0.1–1000 mg/human, preferably 1–500 mg/human, is generally recommended for adults.

Depending on cases, a lower dosage may be sufficient, while a higher dosage may be needed. The above daily dosage can be administered in 2–3 divided doses.

BEST MODE OF CARRYING OUT THE INVENTION

The following examples and test examples of the compound of the invention, and formulation examples of the pharmaceutical composition of the invention are intended to illustrate the present invention in further detail.

REFERENCE EXAMPLE 1

Hederagenin(3β,23-dihydroxyolean-12-en-28-oic acid (compound No. 1)

Dried and ground pericarp of *Sapindus mukorossi* Gaertn. (6.0 kg) was extracted with 60 L of methanol at 70° C. for 2 hours twice and the extract was concentrated under reduced pressure at or below 50° C. to provide 3.88 kg of a methanolic extract.

To 300 g of this methanolic extract was added 1500 ml of 2.5% (v/v) sulfuric acid-methanol and the mixture was refluxed for 2 hours. After this hydrolysis, the reaction mixture was adjusted to pH 6–7 with 5% (w/v) potassium hydroxide-methanol and, with 90 g of activated charcoal added, refluxed for 0.5 hour. The resulting solution was filtered through a uniform bed of celite (2 g) and the filtrate was concentrated under reduced pressure to about 1/10 of the initial volume. To the residue was added 1 L of distilled water and washed under heating and, then, allowed to cool. The residual methanol was distilled off under reduced pressure and the sediment was suction-filtered to provide crude hederagenin.

This crude hederagenin was washed with 1 L of acetonitrile twice and 80 ml of ethanol 3 times under heating to provide 11.05 g of pure hederagenin as white powders.

m.p. 317°–320° C.

Elemental analysis for $C_{30}H_{48}O_4 \cdot 1/4H_2O$ Calcd. (%): C, 75.51; H, 10.24 Found (%): C, 75.49; H, 9.94

IR (KBr) cm$^{-1}$: 3455, 2946, 1698, 1464, 1389, 1038

REFERENCE EXAMPLE 2

Hederagenin sodium salt (sodium 3β,23-dihydroxyolean-12-en-28-oate)

To the hederagenin (1.0 g) obtained in Reference Example 1 was added 1N-sodium hydroxide-methanol solution (2.1 ml) and the mixture was stirred at 50° C. for 2 hours. This reaction mixture was filtered through filter paper to remove insolubles and the filtrate was concentrated to provide the title compound (934 mg).

m.p. 315° C.

Elemental analysis for $C_{30}H_{47}O_4 \cdot Na \cdot 3H_2O$ Calcd. (%): C, 65.67; H. 9.74 Found (%): C, 65.71; H, 9.51

EXAMPLE 1

2-Acetoxyethyl 3β,23(4α)-dihydroxyolean-12-en-28-oate (compound No. 2)

To a solution of hederagenin (473 mg) in DMF (10 ml) was added 2-bromoethyl acetate (334 mg) followed by addition of potassium hydrogen carbonate (200 mg) and the mixture was stirred at 50° C. for 8 hours. This reaction mixture was filtered and concentrated under reduced pressure to remove DMF. The resulting oil was extracted with ethyl acetate and the extract was washed with saturated brine, dried over anhydrous magnesium sulfate ($MgSO_4$), and concentrated under reduced pressure. The residue was purified by silica gel column chromatography (ethyl acetate:n-hexane=1:8) to provide the title compound (490 mg) as colorless crystals.

m.p. 158° C.

Elemental analysis for $C_{34}H_{54}O_6$ Calcd. (%): C, 73.08; H, 9.74 Found (%): C, 72.90; H, 9.64

EXAMPLE 2

Benzyl 3β,23(4α)-dihydroxyolean-12-en-28-oate (compound No. 3)

Using benzyl bromide, the title compound was obtained by the similar method to the procedure of Example 1.

m.p. 159° C.

Elemental analysis for $C_{37}H_{54}O_4 \cdot 1/3H_2O$ Calcd. (%): C, 78.46; H, 9.68 Found (%): C, 78.50; H, 9.47

EXAMPLE 3

2-Methoxyethyl 3β,23(4α)-dihydroxyolean-12-en-28-oate (compound No. 4)

Using 2-bromoethyl methyl ether, the title compound was obtained by the similar method to the procedure of Example 1.

m.p. 161° C.

Elemental analysis for $C_{33}H_{54}O_5 \cdot 1/4H_2O$ Calcd. (%): C, 74.05; H, 10.26 Found (%): C, 74.01; H, 9.92

EXAMPLE 4

2-Hydroxyethyl 3β,23(4α)-dihydroxyolean-12-en-28-oate (compound No. 5)

The compound (1.0 g) obtained in Example 1 was dissolved in methanol (100 ml) followed by addition of aqueous sodium hydroxide solution (5 ml). After the mixture was refluxed at 80° C., methanol was removed. The residue was extracted with ethyl acetate and the extract was dried over anhydrous magnesium sulfate, filtered, and concentrated to provide the title compound as colorless crystals (880 mg).

m.p. 237°–238° C.

Elemental analysis for $C_{32}H_{52}O_5$ Calcd. (%): C, 74.38; H, 10.14 Found (%): C, 74.06, H, 9.90

EXAMPLE 5

3-Bromopropyl 3β,23(4α)-dihydroxyolean-12-en-28-oate hydrochloride (compound No. 6)

Using 1,3-dibromopropane, the title compound was obtained by the similar method to the procedure of Example 1.

EXAMPLE 6

3-N,N-di(2-hydroxyethyl)aminopropyl 3β,23(4α)-dihydroxyolean-12-en-28-oate (compound No. 7)

The crystals (622 mg) obtained in Example 5 were dissolved in DMF (60 ml) followed by addition of diethanolamine (2 ml) and the mixture was stirred at room temperature for 24 hours. This reaction mixture was extracted with ethyl acetate and the extract was dried over anhydrous magnesium sulfate, concentrated, and purified by silica gel column chromatography (ethyl acetate:n-hexane= 3:1). The crystals (580 mg) thus obtained were dissolved in 20% HCl-methanol (20 ml) and the mixture was stirred at room temperature for 30 minutes and concentrated to provide the title compound as colorless crystals (572 mg).

m.p. 267°–268° C.

Elemental analysis for $C_{37}H_{63}NO_6 \cdot HCl \cdot \frac{1}{2}H_2O$ Calcd. (%): C, 66.99; H, 9.88; N, 2.11 Found (%): C, 67.22; H, 9.40; N, 2.33

EXAMPLE 7-(1)

N-(2-methoxyethyl)-3β,23(4α)-diacetoxyolean-12-en-28-amide (compound No. 8)

Step 1  3β,23(4α)-Diacetoxyolean-12-en-28-oic acid

Hederagenin (500 mg) was dissolved in pyridine (20 ml) followed by addition of acetic anhydride (2 ml) and the mixture was stirred at 80° C. for 1 hour. To this was added 1N HCl (5 ml) dropwise and the mixture was stirred for 10 minutes. This reaction mixture was extracted with chloroform (50 ml) three times and the extract was dried over anhydrous magnesium sulfate and the solvent was evaporated off. The residue was purified by silica gel column chromatography (n-hexane:ethyl acetate=4:1) to provide the title compound (580 mg) as white solid.

Step 2  N-(2-methoxyethyl)-3β,23(4α)-diacetoxyolean-12-en-28-amide

To the compound (570 mg) obtained in Step 1 was added thionyl chloride (20 ml) and the mixture was stirred at 70° C. for 1.5 hours. The unreacted thionyl chloride was distilled off under reduced pressure to give a yellow oil. This oil was dissolved in methylene chloride (50 ml) followed by addition of 2-methoxyethylamine (2 ml) and the mixture was stirred at room temperature for 12 hours. This reaction mixture was washed with 1N HCl (50 ml) twice and the organic layer was dried over anhydrous magnesium sulfate. The solvent was then evaporated off to give a yellow solid. This product was purified by silica gel column chromatography (n-hexane:ethyl acetate=4:1→1:1) to provide the title compound (565 mg) as white solid.

EXAMPLE 7-(2)

N-(2-methoxyethyl)-3β,23(4α)-diacetoxyolean-12-en-28-amide (compound No. 8)

Step 1  3β,23(4α)-diacetoxyolean-12-en-28-oic acid

Hederagenin (1.2 g) was dissolved in pyridine (15 ml) followed by addition of acetic anhydride (4 ml) and the mixture was stirred at 70° C. for 1 hour. To this reaction mixture was added 1N HCl (30 ml) dropwise and the mixture was stirred for 10 minutes. The reaction mixture was extracted with ether (20 ml) three times and the extract was dried over anhydrous magnesium sulfate. The solvent was evaporated off and the residue was purified by silica gel column chromatography (n-hexane:ethyl acetate=5:1) to provide the title compound (1.35 g) as white solid.

Step 2  N-(2-methoxyethyl)-3β,23(4α)-diacetoxyolean-12-en-28-amide

The compound (1.2 g) obtained in Step 1 was added thionyl chloride (20 ml) and the mixture was stirred at 80° C. for 1 hour. The unreacted thionyl chloride was then distilled off under reduced pressure to give a yellow oil. To this oil was added 2-methoxyethylamine (330 mg) and the mixture was stirred at room temperature for 1 hour and then extracted with ether. The extract was washed with saturated brine and dried over anhydrous magnesium sulfate. The solvent was then evaporated off to provide the title compound (950 mg) as yellow solid.

EXAMPLE 8-(1)

N-(2-methoxyethyl)-3β,23(4α)-dihydroxyolean-12-en-28-amide (compound No. 9)

The compound (155 mg) obtained in Example 7-(1) was dissolved in methanol (30 ml) followed by addition of 1N aqueous sodium hydroxide solution (10 ml) and the mixture was refluxed for 1 hour. The methanol was distilled off under reduced pressure and the residue was extracted with ethyl acetate (30 ml) three times. The extract was dried over anhydrous magnesium sulfate and the solvent was distilled off. The residue was crystallized from n-hexane/ethyl acetate to provide the title compound (140 mg) as white powders.

m.p. 127°–129° C.

Elemental analysis for $C_{33}H_{55}NO_4 \cdot \frac{3}{5}H_2O$ Calcd. (%): C, 73.32; H, 10.48; N, 2.59 Found (%): C, 73.21; H, 10.24; N, 2.85

EXAMPLE 8-(2)

N-(2-methoxyethyl)-3β,23(4α)-dihydroxyolean-12-en-28-amide (compound No. 9)

The compound (950 mg) obtained in Example 7-(2) was dissolved in methanol (35 ml) followed by addition of 1N aqueous sodium hydroxide (15 ml) and the mixture was stirred at room temperature for 1 hour. The methanol was then distilled off under reduced pressure and the residue was extracted with chloroform. The extract was dried over anhydrous magnesium sulfate and the solvent was distilled off. The residue was recrystallized from ethyl acetate to provide the title compound (830 mg) as white crystals.

m.p. 142°–143° C.

Elemental analysis for $C_{33}H_{55}NO_4 \cdot \frac{3}{5}H_2O$ Calcd. (%): C, 73.32; H, 10.48; N, 2.59 Found (%): C, 73.14; H, 10.25; N, 2.91

EXAMPLE 9

An alternative process for producing N-(2-methoxyethyl)-3β,23(4α)-dihydroxyolean-12-en-28-amide (compound No. 9)

Hederagenin (100 mg), 1-ethyl-3-(3-dimethylaminopropyl)carbodiimide hydrochloride (84 mg), 1-hydroxy-1H-benzotriazole (67 mg), and 2-methoxyethylamine (33 mg) were suspended in DMF (2 ml) and the mixture was stirred at 50° C. for 2 hours. After cooling to room temperature, the reaction mixture was concentrated under reduced pressure. The residue was extracted with ethyl acetate, washed with saturated brine and 1N HCl, dried over anhydrous magnesium sulfate, and concentrated under reduced pressure. The residue was purified by silica gel column chromatography (ethyl acetate:n-hexane=1:10→1:5→1:1) to provide the title compound as colorless crystals (92 mg). The physical data were in agreement with those obtained in Example 8-(2).

EXAMPLE 10

N-(p-fluorophenyl)-3β,23(4α)-diacetoxyolean-12-en-28-amide (compound No. 10)

Using p-fluoroaniline, the title compound was obtained by the similar method to the procedure of Example 7-(1).

EXAMPLE 11

N-(p-fluorophenyl)-3β,23(4α)-dihydroxyolean-12-en-28-amide (compound No. 11)

Using the compound obtained in Example 10, the title compound was obtained by the similar method to the procedure of Example 8-(1).

m.p. 216°–217° C.

EXAMPLE 12

N-[2-(N,N-diethylamino)ethyl]-3β,23(4α)
-diacetoxyolean-12-en-28-amide
(compound No. 12)

Using 2-(N,N-diethylamino)ethylamine, the title compound was obtained by the similar method to the procedure of Example 7-(1).

EXAMPLE 13

N-[2-(N,N-diethylamino)ethyl]-3β,23(4α)
-dihydroxyolean-12-en-28-amide
(compound No. 13)

Using the compound obtained in Example 12, the title compound was obtained by the similar method to the procedure of Example 8-(1).

m.p. 228°–230° C.

Elemental analysis for $C_{36}H_{62}N_2O_3$ Calcd. (%): C, 75.74; H, 10.95; N, 4.91 Found (%): C, 75.74; H, 10.82; N. 5.03

EXAMPLE 14

N-[2-(N,N-diethylamino)ethyl]-3β,23(4α)-
dihydroxyolean-12-en-28-amide hydrochloride
(compound No. 14)

The compound obtained in Example 13 was dissolved in 20% HCl-methanol (20 ml) and the solution was stirred at room temperature for 30 minutes and then concentrated to provide the title compound.

m.p. 263°–265° C.

Elemental analysis for $C_{36}H_{62}N_2O_3.HCl.5/2H_2O$ Calcd. (%): C, 66.28; H, 10.51; N, 4.29 Found (%): C, 66.17; H, 10.30; N, 4.56

EXAMPLE 15

N-[3-[N,N-di(2-hydroxyethyl)amino]propyl]-3β,23
(4α)-diacetoxyolean-12-en-28-amide
(compound No. 15)

Using 3-[N,N-di(2-hydroxyethyl)amino]propylamine, the title compound was obtained by the similar method to the procedure of Example 7-(1).

EXAMPLE 16

N-[3-[N,N-di(2-hydroxyethyl)amino]propyl]-3β,23
(4α)-dihydroxyolean-12-en-28-amide
(compound No. 16)

Using the compound obtained in Example 15, the title compound was obtained by the similar method to the procedure of Example 8-(1).

m.p. 136°–139° C.

Elemental analysis for $C_{37}H_{64}N_2O_5.1/2H_2O$ Calcd. (%): C, 71.00; H, 10.47; N, 4.48 Found (%): C, 70.90; H. 10.26; N, 4.54

EXAMPLE 17

N-[3-[N,N-di(2-hydroxyethyl)amino]propyl]-3β,23
(4α)-dihydroxyolean-12-en-28-amide hydrochloride
(compound No. 17)

Using the compound obtained in Example 16, the title compound was obtained by the similar method to the procedure of Example 14.

m.p. 195° C.

Elemental analysis for $C_{37}H_{64}N_2O_5.HCl.5/3H_2O$ Calcd. (%): C, 65.03; H, 10.08; N, 4.10 Found (%): C, 65.01; H, 9.96; N, 4.19

EXAMPLE 18

N-ethoxycarbonylmethyl-3β,23(4α)-diacetoxyolean-
12-en-28-amide (compound No. 18)

Using glycine ethyl ester hydrochloride, the title compound was obtained by the similar method to the procedure of Example 7-(1).

EXAMPLE 19

N-carboxymethyl-3β,23(4α)-dihydroxyolean-12-en-
28-amide (compound No. 19)

Using the compound obtained in Example 18, the title compound was obtained by the similar method to the procedure of Example 8-(1).

m.p. 187°–190° C.

Elemental analysis for $C_{32}H_{51}NO_5.4/5H_2O$ Calcd. (%): C, 70.63; H, 9.74; N, 2.57 Found (%): C, 70.51; H, 9.38; N, 2.60

EXAMPLE 20

N-ethoxycarbonylmethyl-3β,23(4α)-
dihydroxyolean-12-en-28-amide
(compound No. 20)

The compound (1.1 g) obtained in Example 19 was dissolved in 17% HCl-ethanol (40 ml) and after 2 hours of heating at 80° C. the ethanol was distilled off under reduced pressure. The residue was extracted with chloroform, dried over anhydrous magnesium sulfate, concentrated, and purified by silica gel column chromatography (chloroform:methanol=9:1) to provide 1.1 g of the title compound as colorless crystals.

m.p. 129°–132° C.

Elemental analysis for $C_{34}H_{55}NO_5.2/5H_2O$ Calcd. (%): C, 72.28; H, 9.95; N, 2.48 Found (%): C, 72.29; H, 9.87; N, 2.61

EXAMPLE 21

N-(3-methoxycarbonylpropyl)-3β,23(4α)-
diacetoxyolean-12-en-28-amide (compound No. 21)

Using methyl 4-amino-n-butyrate hydrochloride, the title compound was obtained by the similar method to the procedure of Example 7-(1).

EXAMPLE 22

N-(3-carboxypropyl)-3β,23(4α)-dihydroxyolean-12-
en-28-amide (compound No. 22)

Using the compound obtained in Example 21, the title compound was obtained by the similar method to the procedure of Example 8-(1).

m.p. 203° C.

Elemental analysis for $C_{34}H_{55}NO_5.H_2O$ Calcd. (%): C, 70.92; H, 9.98; N, 2.43 Found (%): C, 71.14; H. 10.01; N, 2.49

EXAMPLE 23

N-(3-ethoxycarbonylpropyl)-3β,23(4α)-
dihydroxyolean-12-en-28-amide
(compound No. 23)

Using the compound obtained in Example 22, the title compound was obtained by the similar method to the procedure of Example 20.

m.p. 108°–110° C.

Elemental analysis for $C_{36}H_{59}NO_5 \cdot 3/10H_2O$ Calcd. (%): C, 73.13; H, 10.16; N, 2.37 Found (%): C, 72.91; H, 10.14; N, 2.35

EXAMPLE 24

N-(2-cyanoethyl)-3β,23(4α)-diacetoxyolean-12-en-28-amide (compound No. 24)

Using 3-aminopropionitrile, the title compound was obtained by the similar method to the procedure of Example 7-(1).

TLC (Merck, Kieselgel 60 $F_{254}$, ethyl acetate:n-hexane=1:1) Rf=0.13

EXAMPLE 25

N-(2-cyanoethyl)-3β,23(4α)-dihydroxyolean-12-en-28-amide (compound No. 25)

Using the compound obtained in Example 24, the title compound was obtained by the similar method to the procedure of Example 8-(1).

EXAMPLE 26

N-[2-(2,4-diamino-1,3,5-triazin-6-yl)ethyl]-3β,23 (4α)-dihydroxyolean-12-en-28-amide (compound No. 26)

A suspension of the compound (550 mg) obtained in Example 25, dicyandiamide (210 mg) and potassium hydroxide (140 mg) in methylcellosolve (50 ml) were refluxed together by heating at 125° C. for 2 hours. The solvent was then distilled off under reduced pressure and the residue was purified by silica gel column chromatography (chloroform→chloroform:methanol=9:1). The crystal crop was washed with hot water and collected in a funnel with a flat perforated plate to provide the title compound as colorless crystals.

m.p. 214° C.

Elemental analysis for $C_{35}H_{56}N_6O_3 \cdot 3/2H_2O$ Calcd. (%): C, 66.11; H, 9.35; N, 13.22 Found (%): C, 65.91; H, 9.16; N, 13.12

EXAMPLE 27

N-(3-methoxypropyl)-3β,23(4α)-diacetoxyolean-12-en-28-amide (compound No. 27)

Using 3-aminopropyl methyl ether, the title compound was obtained by the similar method to the procedure of Example 7-(1).

EXAMPLE 28

N-(3-methoxypropyl)-3β,23(4α)-dihydroxyolean-12-en-28-amide (compound No. 28)

Using the compound obtained in Example 27, the title compound was obtained by the similar method to the procedure of Example 8-(1).

m.p. 83° C.

Elemental analysis for $C_{34}H_{57}NO_4 \cdot 1/4H_2O$ Calcd. (%): C, 74.48; H, 10.57; N, 2.55 Found (%): C, 74.49; H, 10.36; N, 2.90

EXAMPLE 29

Benzyl 3β-hydroxy-23(4α)-benzylolean-12-en-28-oate (compound No. 29)

The compound (3.0 g) obtained in Example 2 was dissolved in DMF (40 ml) followed by addition of sodium hydride (60%, 552 mg), and the mixture was stirred at 0° C. for 1 hour. To this reaction mixture was added benzyl chloride (1.7 g) and the mixture was stirred at room temperature for 2 hours. This reaction mixture was diluted with water and extracted with ethyl acetate and the extract was dried over anhydrous magnesium sulfate, filtered, and concentrated. The residue was purified by silica gel column chromatography (ethyl acetate:n-hexane=1:20) to provide the title compound (3.4 g).

EXAMPLE 30

Benzyl 3β-ethoxycarbonylmethylcarbamoyloxy-23 (4α)- benzylolean-12-en-28-oate (compound No. 30)

The compound (3.4 g) obtained in Example 29, carbonyldiimidazole (3.0 g) and pyridine (50 ml) were stirred together at 80° C. for 20 hours. To this mixture was added glycine ethyl ester hydrochloride (4.3 g) and 4-dimethylaminopyridine (3.8 g), then the mixture was stirred with heating at 80° C. for 20 hours. It was then extracted and concentrated to provide the title compound.

EXAMPLE 31

3β-Ethoxycarbonylmethylcarbamoyloxy-23(4α)-hydroxyolean-12-en-28-oic acid (compound No. 31)

The compound obtained in Example 30 was dissolved in methanol (200 ml) followed by addition of 5% palladium-on-carbon (500 mg), and the mixture was stirred in a hydrogen atmosphere for 24 hours, filtered, and concentrated to provide the title compound.

m.p. 196°–197° C.

Elemental analysis for $C_{35}H_{55}NO_7 \cdot 1/4H_2O$ Calcd. (%): C, 69.33; H, 9.23; N, 2.31 Found (%): C, 69.16; H, 9.04; N, 2.33

EXAMPLE 32

Benzyl 3β-(2-methoxyethyl)carbamoyloxy-23(4α)-benzylolean-12-en-28-oate (compound No. 32)

Using 2-methoxyethylamine, the title compound was obtained as colorless crystals by the similar method to the procedure of Example 30.

EXAMPLE 33

3β-(2-Methoxyethyl)carbamoyloxy-23(4α)-hydroxyolean-12-en-28-oic acid (compound No. 33)

Using the compound obtained in Example 32, the title compound was obtained as colorless crystals by the similar method to the procedure of Example 31.

m.p. 183°–184° C. (recrystallized from ethyl acetate)

Elemental analysis for $C_{34}H_{55}NO_6$ Calcd. (%): C, 71.17; H, 9.66; N, 2.44 Found (%): C, 71.02; H, 9.61; N, 2.56

EXAMPLE 34

3β,23(4α)-Carbonyldioxyolean-12-en-28-oic acid (compound No. 34)

Hederagenin (473 mg) was dissolved in pyridine (10 ml) followed by addition of carbonyldiimidazole (195 mg) and the mixture was heated at 50° C. for 1 hour. This reaction mixture was extracted with ethyl acetate and the organic layer was washed with 1N-hydrochloric acid, dried over anhydrous magnesium sulfate, and concentrated. The residue was purified by silica gel column chromatography (ethyl acetate:n-hexane=1:5) to provide the title compound (423 mg).

m.p. 214°–215° C.

Elemental analysis for $C_{31}H_{46}O_5$ Calcd. (%): C, 74.61; H, 9.32 Found (%): C, 74.36; H, 9.05

EXAMPLE 35

2-Acetoxyethyl 3β-23(4α)-carbonyldioxyolean-12-en-28-oate (compound No. 35)

Using the compound obtained in Example 1, the title compound was obtained by the similar method to the procedure of Example 34.

m.p. 112° C.

Elemental analysis for $C_{35}H_{52}O_7$ Calcd. (%): C, 71.89; H, 8.96 Found (%): C, 71.68; H, 8.86

Presented below are the results of pharmacological tests demonstrating the usefulness of some representative examples of the compound according to the present invention.

Test Example 1
Effect on anti-Thy-1 antibody nephritis in rats

Anti-Thy-1 antibody-induced nephritis is a model of glomerulonephritis constructed by utilizing the reaction between the Thy-1 antigen occurring as a membrane protein of mesangial cells and the antibody to the antigen. In this model, injuries to mesangial cells and lesions associated with mesangial cell proliferation are found. While a large majority of types of chronic glomerulonephritis in human are those of proliferative glomerulonephritis which show mesangial cell proliferation and increases in mesangial matrix as cardinal pathologic features, anti-Thy-1 antibody nephritis is regarded as a model of this human proliferative glomerulonephritis, particularly mesangial proliferative nephritis [Ishizaki et al., Acta. Pathol. Jpn., 36, 1191 (1986)].
(1) Experimental animals
   Rats were used.
(2) Experimental materials
   Preparation of anti-Thy-1 antibody
   Preparation of the antibody was carried out in accordance with the method of Ishizaki et al. referred to above. Thus, an adjuvant suspension of rat thymocytes was prepared and subcutaneously administered to rabbits for immunization. After two booster doses, the blood was collected and the serum separated was subjected to inactivation and absorption to provide an antiserum (anti-Thy-1 antibody).
(3) Experimental procedure
   A predetermined amount of the antiserum was injected intravenously from the tail vein of rats to induce nephritis. Starting the following day after injection, a suspension of the test drug was administered orally once a day for 7 days. On day 8 following the beginning of administration, the animals were sacrificed and the kidneys were removed. The kidney was fixed in 10% phosphate-buffered formalin and, in the routine manner, paraffin sections were prepared and stained with periodic acid-schiff stain for microscopy. For histopathological evaluation, the number of cells in the glomeruli (mainly mesangial cells) in each tissue preparation was counted under a light microscope. Statistical analysis was performed by unpaired t-test. The results are shown in Table 1.

TABLE 1

Histopathological findings of glomeruli

| Test drug | Dose (mg/kg) | n | Number of mesangial cells[a] |
|---|---|---|---|
| Control | Distilled water | 6 | 59.5 ± 3.5 |
| Compound No. 1 | 100 | 5 | 48.2 ± 1.6** |
| Control | Distilled water | 6 | 61.8 ± 2.2 |
| Compound No. 2 | 100 | 5 | 50.9 ± 1.3** |
| Control | Distilled water | 5 | 54.8 ± 2.1 |
| Compound No. 9 | 100 | 5 | 45.8 ± 0.7** |

[a] Number of cells (mesangial cells) per glomerulus
Mean ± standard error (the mean number of cells in the intact animal is 43)
*$P < 0.05$, **$P < 0.01$ It is clear from the above results that the compound of the present invention has inhibitory effect on mesangial cell proliferation in rats with anti-Thy-1 antibody nephritis.

Test Example 2

Effect on nephritis in MRL/lpr mice

The MRL/lpr mouse is a model of lupus nephritis in mice which spontaneously and secondarily develop proliferative glomerulonephritis due to autoimmune disease. Using this nephritis model, a 10-week long-term oral administration experiment with the test drugs was performed.

(1) Experimental animals

MRL/lpr mice purchased from Jackson Laboratory and maintained in Nippon Shinyaku Co., Ltd. were used.

(2) Experimental procedure

A suspension of each test drug was administered orally once a day on 6 days per week from the age 8 weeks for 10 weeks. During the administration period, the semi-quantitative test for urinary protein (regent strips) was performed. At the end of the administration period, the animals were sacrificed and the kidneys were removed. The kidney was fixed in 10% phosphate-buffered formalin and, in the routine manner, paraffin sections were prepared and stained with periodic acid-Schiff stain for microscopy. For histopathological evaluation, the glomerular lesions in each tissue preparation were observed by light microscopy and graded according to the method of Berden (J. Immunology, 130, 1699–1705, 1983) and the incidence (%) of each grade was calculated for each group. Statistical analysis was performed by Mann Whitney's rank-sum test. The results are shown in Tables 2 and 3.

TABLE 2

Incidence of proteinuria
(at 10 weeks of administration)

| Test drug | Dose (mg/kg) | n | Number of animals with proteinuria | | | | |
|---|---|---|---|---|---|---|---|
| | | | − | 1+ | 2+ | 3+ | 4+ |
| Control | 0 | 12 | 0 | 0 | 4 | 1 | 7 |
| Compound No. 1 | 10 | 13 | 0 | 7 | 2 | 1 | 3* |
| Compound No. 1 | 30 | 14 | 3 | 4 | 0 | 5 | 2* |

−: negative, 1+: 30–100 mg/dl, 2+: 100–300 mg/dl, 3+: 300–1000 mg/dl, 4+: >1000 mg/dl, *$P < 0.05$

TABLE 3

Histopathological findings of glomeruli
(the incidence of glomerular lesions)

| Test drug | Dose (mg/kg) | — | 1+ | Incidence (%) of glomerular lesions 2+ | 3+ | 4+ |
|---|---|---|---|---|---|---|
| Control | 0 | 1 | 14 | 52 | 25 | 8 |
| Compound No. 1 | 10 | 3 | 29 | 57 | 9 | 2** |
| Compound No. 1 | 30 | 3 | 25 | 63 | 9 | 0** |

—: no remarkable change, 1+: slight change, 2+: moderate change, 3+: marked change, 4+: extremely marked change, **$P < 0.01$ It is clear from the above results that the compound of the present invention has inhibitory effects on urinary protein and progression of pathological changes of renal tissues in the MRL/lpr mouse which is a model of lupus nephritis.

Test example 3
Inhibitory effect on mesangial cell proliferation in vitro
(1) Experimental materials and methods Glomeruli were isolated from the rat kidney by the sieving method. Mesangial cells were obtained from isolated these glomeruli which were maintained in culture. The mesangial cells were seeded on the plate and, after 24 hours, an LPS (lipopolysaccharide)-stimulated macrophage culture supernatant (a solution containing growth factor) and the test drug were added and the plate was incubated for 72 hours. The mesangial cells were fixed and stained with crystal violet and the absorbance was measured. The inhibitory activity of the mesangial cell proliferation of the test compound was evaluated in relative inhibition rate (%) in comparison with the absorbance of the control obtained under the same culture conditions. The results are shown in Table 4.

TABLE 4

The inhibitory activity of mesangial cell proliferation in vitro

| Test drug | Dose (μg/ml) | Inhibition rate (%) |
|---|---|---|
| Compound No. 2 | 10 | 57.9 |
| Compound No. 9 | 10 | 43.3 |

It is clear from the above results that the compound of the present invention has inhibitory activity of mesangial cell proliferation in vitro.

Test Example 4
Acute toxicity

A suspension of the test drug was administered orally in a dose of 2 g/kg to mice and the animals were observed for general condition up to 1 week later. Compound No. 1 and the compound No. 9 were examined.

As a result, no death was encountered, nor was there any abnormal findings, in any dose group.

Formulation Example 1

| Tablets (oral tablets) In 80 mg per tablet, | |
|---|---|
| Compound of compound No. 1 | 5.0 mg |
| Corn starch | 46.6 mg |
| Crystalline cellulose | 24.0 mg |
| Methylcellulose | 4.0 mg |
| Nagnesium stearate | 0.4 mg |

The above mixed powder is compressed to provide oral tablets.

Formulation Example 2

| Tablets (oral tablets) In 80 mg per tablet, | |
|---|---|
| Compound of compound No. 2 | 5.0 mg |
| Corn starch | 46.6 mg |
| Crystalline cellulose | 24.0 mg |
| Methylcellulose | 4.0 mg |
| Magnesium stearate | 0.4 mg |

The above mixed powder is compressed to provide oral tablets.

Formulation Example 3

| Tablets (oral tablets) In each 80 mg per tablet, | |
|---|---|
| Compound of compound No. 9 | 5.0 mg |
| Corn starch | 46.6 mg |
| Crystalline cellulose | 24.0 mg |
| Methylcellulose | 4.0 mg |
| Magnesium stearate | 0.4 mg |

The above mixed powder is compressed to provide oral tablets.

INDUSTRIAL APPLICABILITY

As described above, the compound of the present invention has excellent mesangial cell proliferation inhibitory activity, and showing efficacy in animal models of nephritis and being low in toxicity, it is useful for the therapy of nephritis.

We claim:
1. A method for treating an animal suffering from nephritis, which comprises administering to the sufferer an effective amount of a compound of formula (1) or a pharmaceutically acceptable salt thereof, or a solvate of said compound or said salt:

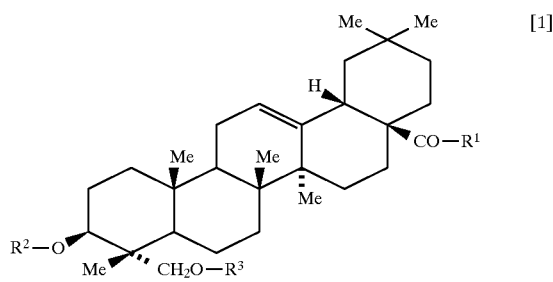

wherein $R^1$ is $OR^{11}$ or $NR^{11}R^{12}$, $R^{11}$ and $R^{12}$ are the same or different and each is (1) hydrogen, (2) alkyl optionally substituted, (3) cycloalkyl optionally substituted, (4) alkenyl optionally substituted, (5) alkynyl optionally substituted, (6) aryl optionally substituted, or (7) a heteroaromatic group optionally substituted;

$R^2$ and $R^3$ is the same or different and each is (1) hydrogen, (2) alkyl optionally substituted, (3) cycloalkyl optionally substituted, (4) alkenyl optionally substituted, (5) alkynyl optionally substituted, (6) acyl optionally substituted, (7) monoalkylcarbamoyl optionally substituted, (8) dialkylcarbamoyl optionally substituted, or (9) alkoxy carbonyl optionally substituted, or $R^2$ and $R^3$ taken together is carbonyl;

wherein the substituents on $R^{11}$, $R^{12}$, $R^2$, $R^3$ are the same or different and are selected from (1) halogen, (2) $OR^{13}$, (3) $OCOR^{13}$, (4) $COOR^{13}$, (5) cyano, (6) $NR^{13}R^{14}$, (7) cycloalkyl, (8) aryl optionally substituted by halogen, alkyl, hydroxy, or amino, and (9) a heteroaromatic group optionally substituted by halogen, alkyl, hydroxy, or amino;

wherein $R^{13}$ and $R^{14}$ are the same or different and each is (1) hydrogen or (2) alkyl optionally substituted by hydroxy, alkoxy, amino, monoalkylamino, or dialkylamino.

2. The method of claim 1, wherein $R^1$ is hydroxy, acyloxyalkoxy, phenylalkoxy, alkoxyalkoxy, hydroxyalkoxy, haloalkoxy, di(hydroxyalkyl)aminoalkoxy, (alkoxyalkyl)amino, halogen-substituted phenylamino, (dialkylaminoalkyl)amino, [di(hydroxyalkyl)aminoalkyl]amino, (carboxyalkyl)amino, (alkoxycarbonylalkyl)amino, (cyanoalkyl)amino, or diamino-substituted triazinylalkylamino, $R^2$ is hydrogen, and $R^3$ is hydrogen.

3. The method of claim 1, wherein $R^1$ is hydroxy, (alkoxyalkyl)amino, halogen-substituted phenylamino, (dialkylaminoalkyl)amino, [di(hydroxyalkyl)aminoalkyl]amino, (alkoxycarbonylalkyl)amino, or (cyanoalkyl)amino, $R^2$ is acetoxy, and $R^3$ is acetoxy.

4. The method of claim 1, wherein $R^1$ is phenylalkoxy, $R^2$ is hydroxy, (alkoxycarbonylalkyl)carbamoyl, or (alkoxyalkyl)carbamoyl, and $R^3$ is phenylalkyl.

5. The method of claim 1, wherein $R^1$ is hydroxy, $R^2$ is (alkoxycarbonylalkyl)carbamoyl, or (alkoxyalkyl)carbamoyl, and $R^3$ is hydrogen.

6. The method of claim 1, wherein $R^1$ is hydroxy or acyloxyalkoxy, and $R^2$ and $R^3$ taken together is carbonyl.

7. The method of claim 1, wherein $R^1$ is hydroxy, 2-methoxyethylamino, or 2-acetoxyethoxy, $R^2$ is hydrogen, and $R^3$ is hydrogen.

8. The method of claim 1, wherein said nephritis is proliferative glomulonephritis.

9. The method of claim 1, wherein said nephritis is chronic nephritis.

10. The method of claim 1, wherein the animal is a human.

11. A compound of formula (1) or a pharmaceutically acceptable salt thereof, or a solvate of said compound or said salt:

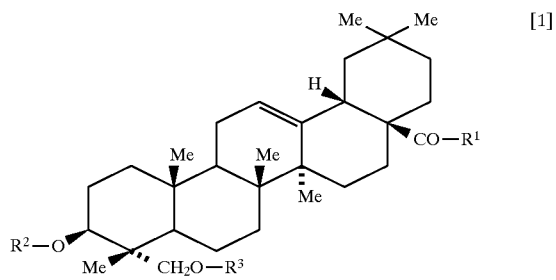

wherein $R^1$ is $OR^{11}$ or $NR^{11}R^{12}$, $R^{11}$ and $R^{12}$ are the same or different and each is (1) hydrogen, (2) alkyl optionally substituted, (3) cycloalkyl optionally substituted, (4) alkenyl optionally substituted, (5) alkynyl optionally substituted, (6) aryl optionally substituted, or (7) a heteroaromatic group optionally substituted;

$R^2$ and $R^3$ may be the same or different and each is (1) hydrogen, (2) alkyl optionally substituted, (3) cycloalkyl optionally substituted, (4) alkenyl optionally substituted, (5) alkynyl optionally substituted, (6) acyl optionally substituted, (7) monoalkylcarbamoyl optionally substituted, (8) dialkylcarbamoyl optionally substituted, or (9) alkoxy-carbonyl optionally substituted, or $R^2$ and $R^3$ taken together is carbonyl;

wherein the substituents on $R^{11}$, $R^{12}$, $R^2$, $R^3$ are the same or different and are selected from (1) halogen, (2) $OR^{13}$, (3) $OCOR^{13}$, (4) $COOR^{13}$, (5) cyano, (6) $NR^{13}R^{14}$, (7) cycloalkyl, (8) aryl optionally substituted by halogen, alkyl, hydroxy, or amino, and (9) a heteroaromatic group optionally substituted by halogen, alkyl, hydroxy, or amino;

wherein $R^{13}$ and $R^{14}$ may be the same or different and each is (1) hydrogen or (2) alkyl optionally substituted by hydroxy, alkoxy, amino, monoalkylamino, or dialkylamino but exclusive of the compounds wherein $R^1$ is hydroxy or methoxy; $R^2$ and $R^3$ are the same or different and each is hydrogen, methyl, formyl, acetyl or benzoyl.

12. The compound, pharmaceutically acceptable salt, or solvate claimed in claim 11 wherein $R^1$ is hydroxy, acyloxyalkoxy, phenylalkoxy, alkoxyalkoxy, hydroxyalkoxy, haloalkoxy, di(hydroxyalkyl)aminoalkoxy, (alkoxyalkyl)amino, halogen-substituted phenylamino, (dialkylaminoalkyl)amino, [di(hydroxyalkyl)aminoalkyl]amino, (carboxyalkyl)amino, (alkoxycarbonylalkyl)amino, (cyanoalkyl)amino, or diamino-substituted triazinylalkylamino, $R^2$ is hydrogen, and $R^3$ is hydrogen.

13. The compound, pharmaceutically acceptable salt, or solvate claimed in claim 11 wherein $R^1$ is hydroxy, (alkoxyalkyl)amino, halogen-substituted phenylamino, (dialkylaminoalkyl)amino, [di(hydroxyalkyl)aminoalkyl]amino, (alkoxycarbonylalkyl)amino, or (cyanoalkyl)amino, $R^2$ is acetoxy, and $R^3$ is acetoxy.

14. The compound, pharmaceutically acceptable salt, or solvate claimed in claim 11 wherein $R^1$ is phenylalkoxy, $R^2$ is hydroxy, (alkoxycarbonylalkyl)carbamoyl, or (alkoxyalkyl)carbamoyl, and $R^3$ is phenylalkyl.

15. The compound, pharmaceutically acceptable salt, or solvate claimed in claim 11 wherein $R^1$ is hydroxy, $R^2$ is (alkoxycarbonylalkyl)carbamoyl, or (alkoxyalkyl)carbamoyl, and $R^3$ is hydrogen.

16. The compound, pharmaceutically acceptable salt, or solvate claimed in claim 11 wherein $R^1$ is hydroxy or acyloxyalkoxy, and $R^2$ and $R^3$ taken together is carbonyl.

17. The compound, pharmaceutically acceptable salt, or solvate claimed in claim 11 wherein $R^1$ is 2-methoxyethylamino or 2-acetoxyethoxy, $R^2$ is hydrogen, and $R^3$ is hydrogen.

18. A pharmaceutical composition for the treatment of an animal, including humans, suffering from nephritis, which comprises an effective amount of the compound, pharmaceutically acceptable salt or solvate of claim 11 and a pharmaceutically acceptable carrier therefor.

* * * * *